United States Patent [19]
DellaPenna et al.

[11] Patent Number: 6,087,563
[45] Date of Patent: Jul. 11, 2000

[54] CLONED ARABIDOPSIS P-HYDROXYPHENYL PYRUVIC ACID DIOXYGENASE DNA

[75] Inventors: Dean DellaPenna, Reno, Nev.; Susan R. Norris, Tucson, Ariz.

[73] Assignee: Arizona Board of Regents on Behalf of the University of Arizona, Tucson, Ariz.

[21] Appl. No.: 08/592,900

[22] Filed: Jan. 29, 1996

[51] Int. Cl.[7] .............................. A01H 5/00; A01H 5/10; C12N 1/21; C12N 5/14; C12N 15/29; C12N 15/52; C12N 15/82

[52] U.S. Cl. .................. 800/317.4; 435/243; 435/252.3; 435/320.1; 435/419; 536/23.2; 536/23.6; 800/278; 800/298

[58] Field of Search .............................. 435/172.3, 320.1, 435/252.3, 243, 419, 468; 536/23.1, 23.2, 23.6; 800/205, 250, 278, 298, 317.4

[56] References Cited

PUBLICATIONS

Smith et al. Antisense RNA inhibition of polygalacturonase gene expression in transgenic tomatoes. Nature. 334:724–726, 1988.

Napoli et al. Introduction of a chimeric chalcone synthase gene into petunia results in reversible co–suppression of homologous genes in trans. The Plant Cell. 2:279–289, 1990.

Endo et al. Primary structure deduced from complementary DNA sequence and expression in cultured cells of mammalian 4–hygroxyphenylpyruvic acid dioxygenase. The Journal of Biological Chemistry. 267(34):24235–24240, 1992.

Newman et al. Genes galore: a summary of methods for accessing results from large–scale partial sequencing of anonymous Arabidopsis cDNA clones. Plant Physiology. 106:1241–1255, 1994.

MPSEARCH results 1 and 2 of SEQ ID No:1: Locus N65764, Accession No. N65764. Newman et al., as above, 1994.

MPSEARCH Result 2 of SEQ ID NO:2: Locus PIGHPD, Accession No. D13390. Endo et al., as above, 1992.

Coon, Steven L., et al., "Homogentisic Acid is the Product of MeIA, Which Mediates Melanogenesis in the Marine Bacterium *Shewanella colwelliana* D†," *Applied and Environmental Microbiology* vol. 60, No. 8: 3006–3010 (1994).

Goodwin, P.H., et al., "Brown pigmentation of *Xanthomonas campestris* pv. *phaseoli* associated with homogentistic acid," *Can. J. Microbiol.* 40:28–34 (1994).

Misawa, Norihiko, et al., "Functional expression of the *Erwinia uredovora* carotenoid biosynthesis gene crtI in transgenic plants showing an increase of β–carotene biosynthesis activity and resistance to bleaching herbicide norflurazon," *The Plant Journal* 4:833–840 (1993).

Norris, Susan, et al., Poster Presented at Gordon Conference on Carotenoids, Ventura, California Doubletree Hotel (Feb. 5–9, 1995).

Norris, Susan R., et al., "Genetic Dissection of Carotoid Synthesis in Arabidopsis Defines Plastoquinone as an Essential Component of Phytoene Desaturation," *The Plant Cell* 7:2139–2149 (1995).

Ruetschi, Ulla, et al., "Characterization of 4–hydroxyphenylpyruvate dioxygenase: Primary structure of the Pseudomonas enzyme," *Eur. J. Biochem.*, 205:459–466 (1992).

Schultz, Arno, et al., "SC–0051, a 2–benzoyl–cyclohexane–1,3–dione bleaching herbicide, is a potent inhibitor of the enzyme p–hydroxyphenylpyruvate dioxygenase," *FEBS 12117* 318:162–166 (1993).

Secor, Jacob, "Inhibition of Barnyardgrass 4–hydroxyphenylpyruvate Dioxygenase by Sulcotrione," *Plant Physiol.* 106:1429–1433 (1994).

Soeda, Takashi, et al., "Inhibition of Pigment Synthesis by 1,3–Dimethyl–4–(2, 4–dichlorobenzoyl)–5–hydroxypyrazole, Norflurazon, and New Herbicidal Compounds in Radish and Flatsedge Plants," *Pesticide Biochemistry and Physiology* 29:35–42 (1987).

Watson, C.F., et al., "Antisense RNA in Plants," *Trangenic Plants* 255–281 (1993).

*Primary Examiner*—Amy Nelson
*Attorney, Agent, or Firm*—Quarles & Brady LLP

[57] ABSTRACT

A cDNA clone from *Arabidopsis thaliana*, pHPP1.5, SEQ ID NO:1, which encodes the enzyme p-hydroxyphenyl pyruvic acid dioxygenase, is disclosed. A vector and microbial host containing a DNA sequence coding for the expression of *Arabidopsis thaliana* p-hydroxyphenyl pyruvic acid dioxygenase, and a genetic construct containing a DNA sequence coding for the expression of *Arabidopsis thaliana* p-hydroxyphenyl pyruvic acid dioxygenase, together with a promoter located 5' to the DNA coding sequence and a 3' termination sequence, are also disclosed. A method of creating a transgenic plant comprising said genetic construct is also disclosed.

16 Claims, 6 Drawing Sheets

CLONED ARABIDOPSIS P-HYDROXYPHENYL PYRUVIC ACID DIOXYGENASE DNA

This invention was made with Government support under Grant Number 93373069083 awarded by the U.S. Department of Agriculture. The Government has certain rights in the invention.

FIELD OF THE INVENTION

The present invention relates to a molecular approach for modifying the synthesis of vitamin E, plastoquinone, and carotenoids in plants by use of a full-length cloned cDNA which encodes a p-hydroxyphenyl pyruvic acid dioxygenase enzyme.

BACKGROUND OF THE INVENTION

The chloroplasts of higher plants contain many unique, interconnected biochemical pathways that produce an array of secondary metabolite compounds which not only perform vital functions within the plant but are also important from agricultural and nutritional perspectives. Three such secondary metabolites are the lipid soluble, chloroplastically synthesized compounds vitamin E (α-tocopherol or α-toc), plastoquinones (PQ), and carotenoids, which together perform many crucial biochemical functions in the chloroplast. PQ and vitamin E are quinone compounds synthesized by a common pathway in the plastid; carotenoids are tetraterpenoids synthesized by a separate plastid-localized pathway.

Plastoquinone (PQ) often accounts for up to 50% of the total plastidic quinone pool in green tissues. The primary function of PQ is as a fundamental component of the photosynthetic electron transport chain, acting as an electron carrier between photosystem II and the cytochrome $b_6f$ complex. PQ likely has other less well studied functions in plastids, namely in acting as a direct or intermediate electron carrier for a variety of other biosynthetic reactions in the chloroplast.

Vitamin E is the second major class of chloroplastic quinones, accounting for up to 40% of the quinone pool in plastids. The essential nutritional value of tocopherols was recognized around 1925, and the compound responsible for Vitamin E activity was first identified as α-tocopherol in 1936. α-Toc has a well-documented role in mammals as an antioxidant, and a similar, though less well understood antioxidant role in plants. Liebler, et al., *Toxicology* 23:147–169, 1993; Hess, *Anti-oxidants in Higher Plants*, CRC Press: 111–134, 1993.

Carotenoids are a separate, diverse group of lipophilic pigments synthesized in plants, fungi, and bacteria. In photosynthetic tissues, carotenoids function as accessory pigments in light harvesting and play important roles in photoprotection by quenching free radicals, singlet oxygen, and other reactive species. Siefermann-Harms, *Physiol. Plantarum*. 69:561–568, 1987. In the plastids of non-photosynthetic tissues, high levels of carotenoids often accumulate providing the intense orange, yellow, and red coloration of many fruits, vegetables, and flowers (Pfander, *Methods in Enzym.*, 213A, 3–13, 1992). In addition to their many functions in plants, carotenoids and their metabolites also have important functions in animals, where they serve as the major source of Vitamin A (retinol), and have been identified as providing protection from some forms of cancer due to their antioxidant activities. Vitamin E's antioxidant activities are also thought to protect against some forms of cancer, and may act synergistically with carotenoids in this regard. Liebler, et al., *Toxicology* 23:147–169, 1993; Krinsky, *J. Nutr.* 119:123–126, 1989.

Figure 1:
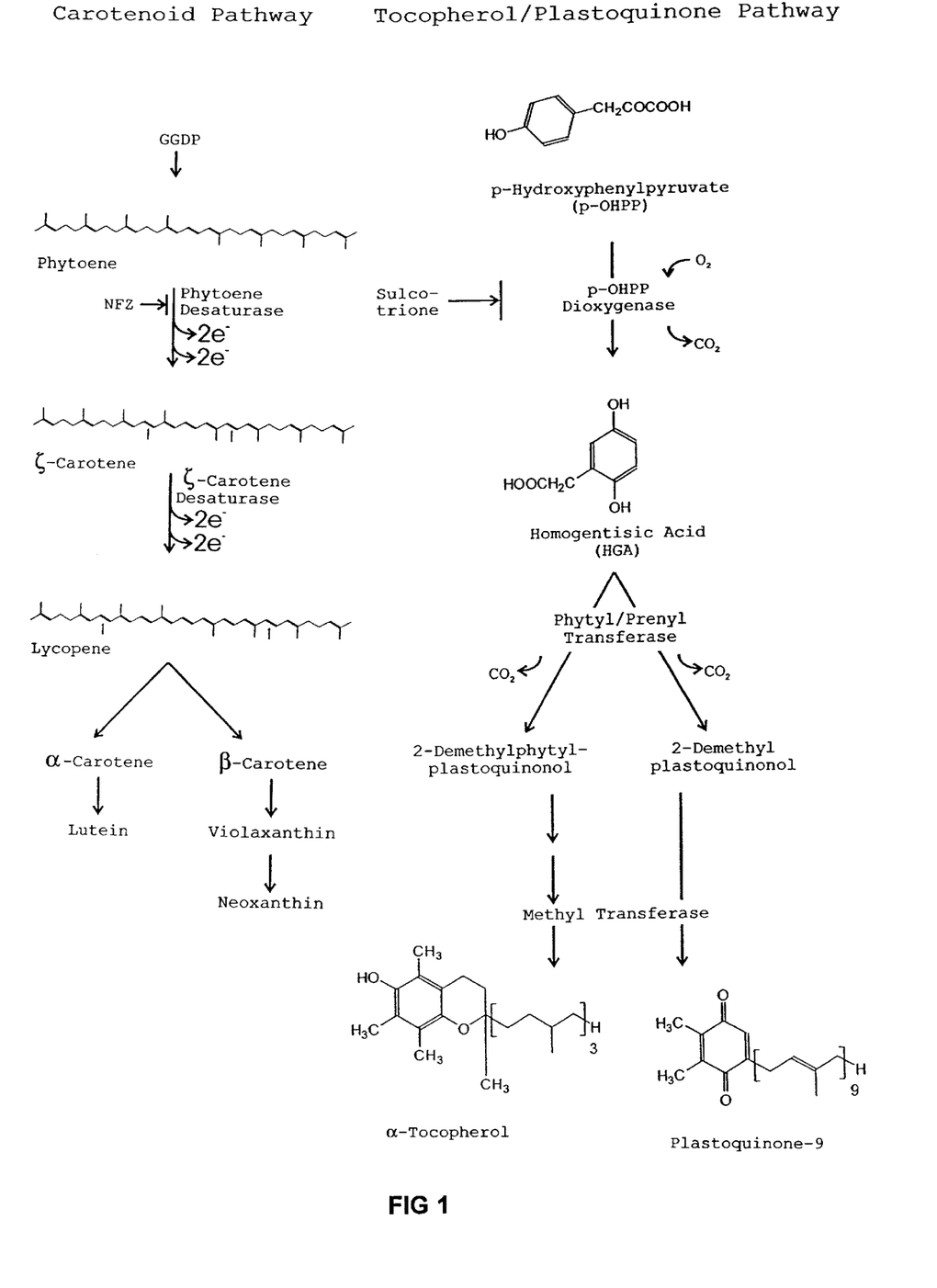
FIG. 1 is a diagram of the pathways for synthesis of carotenoids, vitamin E (tocopherol), and plastoquinone.

Tocopherol and Plastoquinone Synthesis

α-Tocopherol and plastoquinone are the most abundant quinones in the plastid and are synthesized by the common pathway shown in FIG. 1. The precursor molecule for both compounds, homogentisic acid (HGA), is produced in the chloroplast from the shikimic acid pathway intermediate p-hydroxyphenyl pyruvic acid (pOHPP), in an oxidation/decarboxylation reaction catalyzed by the enzyme p-hydroxyphenyl pyruvic acid dioxygenase (pOHPP dioxygenase). Homogentisic acid is subject to phytylation/prenylation (phytylpyrophosphate and solanylpyrophosphate, $C_{20}$ and $C_{45}$, respectively) coupled to a simultaneous decarboxylation by a phytyl/prenyl transferase to form the first true tocopherol and plastoquinone intermediates, 2-demethylphytylplastoquinol and 2-demethylplastoquinol-9, respectively. A single ring methylation occurs on 2-demethylplastoquinol to yield plastoquinol-9 ($PQH_2$) which is then oxidized to plastoquinone-9 (PQ). This oxidation is reversible and is the basis of electron transport by plastoquinone in the chloroplast.

The preferred route, as established in spinach, for α-tocopherol formation from 2-demethylphytylplastoquinol appears to be 1) ring methylation of the intermediate, 2-α-demethylphytylplastoquinol, to yield phytylplastoquinol, 2) cyclization to yield d-tocopherol and, finally, 3) a second ring methylation to yield α-tocopherol. Ring methylation in both tocopherol and plastoquinone synthesis is carried out by a single enzyme that is specific for the site of methylation on the ring, but has relatively broad substrate specificity and accommodates both classes of quinone compounds. This methylation enzyme is the only enzyme of the pathway that has been purified from plants to date. d'Harlingue, et al., *J.Biol.Chem.* 26:15200, 1985. All enzymatic activities of the α-toc/PQ pathway have been localized to the inner chloroplast envelope by cell fractionation studies except for pOHPP dioxygenase and the tocopherol cyclase enzyme. Difficulties with cell fractionation methods, low activities for some of the enzymes, substrate stability and availability and assay problems, make studying the pathway biochemically difficult.

Vitamin E and PQ levels, ratios, and total amounts vary by orders of magnitude in different plants, tissues and developmental stages. Such variations indicate that the vitamin E and PQ pathway is both highly regulated and has the potential for manipulation to modify the absolute levels and ratios of the two end products. The pathway in FIG. 1 makes it clear that production of homogentisic acid by pOHPP dioxygenase is likely to be a key regulatory point for bulk flow through the pathway, both because HGA production is the first committed step in α-toc/PQ synthesis, and also because the reaction is essentially irreversible. Therefore modifying the levels of HGA by modifying pOHPP dioxygenase activity should have a direct impact on the total α-toc/PQ biosynthetic accumulation in plant tissues, and, as described below, because of the connection of PQ and carotenoid synthesis, should also affect carotenoid synthesis in plant tissues.

Carotenoid Biosynthesis; Quinones as Electron Carriers

In plants, carotenoids are synthesized and accumulate exclusively in plastids via the pathway shown on the left-hand side of FIG. 1. The first committed step in carotenoid synthesis is the condensation of two molecules of the $C_{20}$ hydrocarbon geranylgeranyl pyrophosphate (GGDP) by the enzyme phytoene synthase, to form the colorless $C_{40}$ hydrocarbon, phytoene. In oxygenic photosynthetic organisms (e.g. plants, algae, and cyanobacteria), phytoene undergoes two sequential desaturation reactions, catalyzed by phytoene desaturase, to produce ζ-carotene through the intermediate phytofluene. Subsequently, ζ-carotene undergoes two further desaturations, catalyzed by ζ-carotene desaturase, to yield the red pigment lycopene. Lycopene is cyclized to produce either α-carotene or β-carotene, both of which are subject to various hydroxylation and epoxidation reactions to yield the carotenoids and xanthophylls most abundant in photosynthetic tissues of plants, lutein, β-carotene, violaxanthin and neoxanthin.

The genes encoding the first two enzymes of the carotenoid pathway (phytoene synthase and phytoene desaturase) have been isolated and studied from a number of plant and bacterial sources in recent years. Sandmann, *Eur. J. Biochem.* 223:7–24, 1994. Phytoene desaturase has been the most intensively studied, both because it is a target for numerous commercially important herbicides, and also because the phytoene desaturation reaction is thought to be a rate limiting step in carotenoid synthesis. Molecular and biochemical studies suggest that two types of phytoene desaturase enzymes have evolved by independent evolution: the crtI-type found in anoxygenic photosynthetic organisms (e.g. Rhodobacter and Erwinia), and the pds-type found in oxygenic photosynthetic organisms. Despite their differences in primary amino acid sequence, all phytoene desaturase enzymes contain a dinucleotide binding domain (FAD or NAD/NADP), which in *Capsicum annuum* has been shown to be FAD. Hugueney et al., *Eur. J. Biochem.* 209:399–407, 1992. Presumably, the bound dinucleotide in both types of phytoene desaturase enzymes is reduced during desaturation and reoxidized by an unknown reductant present in the plastid or bacterium.

Several lines of evidence have suggested a role for quinones in the phytoene desaturation reaction in higher plants. Using isolated daffodil chromoplasts, Mayer and co-workers demonstrated that in an anaerobic environment, oxidized artificial quinones were required for the desaturation of phytoene while reduced quinones were ineffective. Mayer et al., *Eur. J. Biochem.* 191:359–363, 1990. Further supporting evidence comes from studies with the triketone class of herbicides (e.g. Sulcotrione), which cause phytoene accumulation in treated tissues but unlike the well-studied pyridazone class (e.g. Norflorazon (NFZ)) do not directly affect the phytoene desaturase enzyme. Rather, triketone herbicides competitively inhibit pOHPP dioxygenase, an enzyme common to the synthesis of both plastoquinone and tocopherols, suggesting that one or more classes of quinones may play a role in carotenoid desaturation reactions. Schulz et al., *FEBS* 318:162–166, 1993; Secor, *Plant Physiol.* 106: 1429–1433; Beyer et al., *IUPAC Pure and Applied Chemistry* 66:1047–1056, 1994.

Despite the well-studied, wide-spread importance of vitamin E, plastoquinone, and carotenoids to human nutrition, agriculture, and biochemical processes within plant cells, much remains unclear about their biosynthesis and accumulation in plant tissues. This uncertainty has in turn limited the potential for manipulation of the synthesis and levels of these important compounds in plants.

SUMMARY OF THE INVENTION

In one embodiment, this invention provides a biologically pure sample of DNA which DNA comprises a sequence coding for the expression of *Arabidopsis thaliana* p-hydroxyphenyl pyruvic acid dioxygenase.

In other embodiments, this invention provides a vector and microbial host containing a DNA sequence sufficiently homologous to SEQ ID NO:1 so as to code for the expression of Arabidopsis thaliana p-hydroxyphenyl pyruvic acid dioxygenase, and a genetic construct containing a DNA sequence sufficiently homologous to SEQ ID NO:1 so as to code for the expression of Arabidopsis thaliana p-hydroxyphenyl pyruvic acid dioxygenase, together with a promoter located 5' to the DNA coding sequence and a 3' termination sequence.

In another embodiment, this invention provides a method of creating a transgenic plant in which the levels of the pOHPP dioxygenase enzyme are elevated sufficient such that production of plastoquinones, vitamin E, and carotenoids are modified.

It is an object of the present invention to genetically engineer higher plants to modify the production of plastoquinones, vitamin E, and carotenoids.

It is another object of the invention to provide transgenic plants that would express elevated levels of the pOHPP dioxygenase enzyme which would have resultant elevated resistance to the triketone class of herbicides (i.e. sulcotrione).

It is another object of the present invention to provide a method for the preparation of the enzyme p-hydroxyphenyl pyruvic acid dioxygenase (pOHPP dioxygenase), an enzyme which can be used to identify new pOHPPdioxygenase-inhibiting herbicides.

Other features and advantages of the invention will be apparent from the following description of the preferred embodiments thereof and from the claims.

DETAILED DESCRIPTION OF THE INVENTION

As described above, both Vitamin E, plastoquinones and carotenoids are synthesized and accumulated in plastids by the pathways shown in FIG. 1. This specification describes the identification, isolation, characterization and functional analysis of a higher plant pOHPP dioxygenase cDNA, its role in α-toc, PQ and carotenoid synthesis, and the use of this cDNA to modify pOHPP dioxygenase activity in plant tissues and hence the accumulation of one or more of the compounds plastoquinones, vitamin E, and carotenoids in plant tissues. The overexpression of pOHPP dioxygenase in transgenic plants will modify the enzyme-to-inhibitor ratio of plant tissues exposed to triketone herbicides, as compared to non-transgenic plants, resulting in increased herbicide resistance. The present specification also describes a genetic construct for use in the production of pOHPP dioxygenase, an enzyme useful in identifying new pOHPP dioxygenase-inhibiting herbicides.

Figure 2:
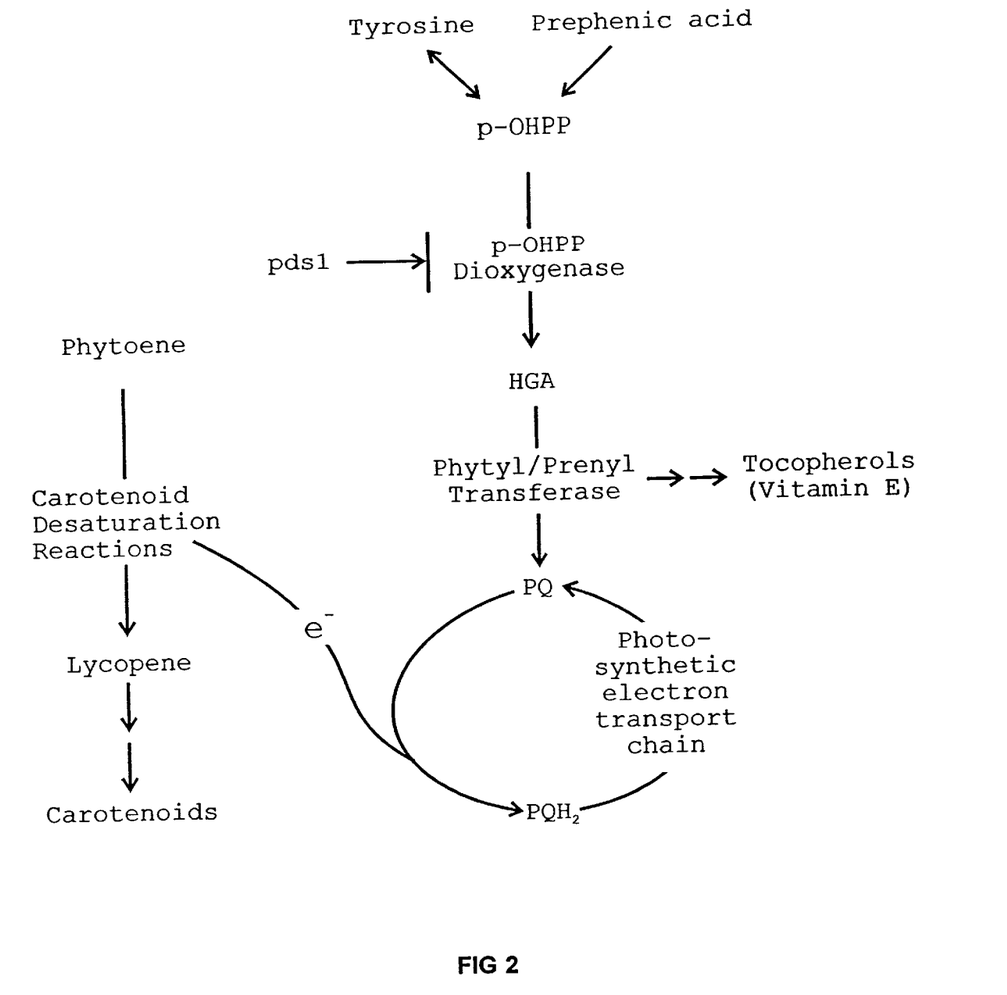
FIG. 2 is a diagram of the interconnections of the pathways illustrated in FIG. 1.

By genetic analysis the present inventors have shown that the vitamin E, plastoquinone, and carotenoid biosynthetic pathways are interconnected and share common elements as shown in FIG. 2. From mutational studies in *Arabidopsis thaliana*, the present inventors identified one genetic locus, designated pdsl (pds=phytoene desaturation), the disruption of which results in accumulation of the first carotenoid of the carotenoid biosynthetic pathway, phytoene. Surprisingly, though this mutation disrupts carotenoid synthesis and was originally identified on this basis, it does not map to the locus encoding the phytoene desaturase enzyme. Evidence indicates that pds1 defines a second gene product in addition to the phytoene desaturase enzyme, necessary for phytoene desaturation and hence carotenoid synthesis in higher plants. This gene product proved to be pOHPP dioxygenase.

To provide a molecular mechanism for manipulating synthesis and accumulation of the compounds plastoquinone, vitamin E, and carotenoids, the present inventors used a molecular genetic approach, taking advantage of the model plant system *Arabidopsis thaliana* to define, isolate and study genes required for synthesis of the compounds in plants. The flowering plant *Arabidopsis thaliana* has come into wide use as a model system to explore the molecular biology and genetics of plants. Arabidopsis offers many advantages for genetic analysis: it can be selfed and very large numbers of progeny can be obtained (up to 10,000 seeds from a single plant). Furthermore, Arabidopsis has a short generation time of five to six weeks, so crosses can be set up and the progeny analyzed within reasonable periods of time. Mutation screens have identified thousands of mutations affecting many aspects of basic plant biology, including morphogenesis, photosynthesis, fertility, starch and lipid metabolism, mineral nutrition, an so on. In addition, its haploid genome is only about $10^8$ base pairs.

An important aspect of the successful approach used here is that essential components were first functionally defined genetically, prior to their isolation, analysis and molecular manipulation. Briefly, potential mutants were identified by a combination of phenotypic and biochemical screening, characterized at the genetic and molecular levels, loci of interest selected, and the corresponding genes then cloned and studied further. By this approach, the inventors genetically defined and isolated cDNAs for one gene, pds1, whose mutation disrupts synthesis of all three classes of compounds in the plastid, tocopherols, plastoquinones and carotenoids. Based on biochemical analysis of the pds1 mutant, the pds1 gene was identified as affecting the activity of pOHPP dioxygenase, a crucial enzyme of the plastidic quinone pathway in plants (FIG. 1), that is directly required for the synthesis of plastoquinone and α-tocopherol and indirectly for carotenoid synthesis. In particular, the deduced function of the pds1 mutant and pOHPP dioxygenase enzyme are noted in FIG. 2.

Figure 5A:
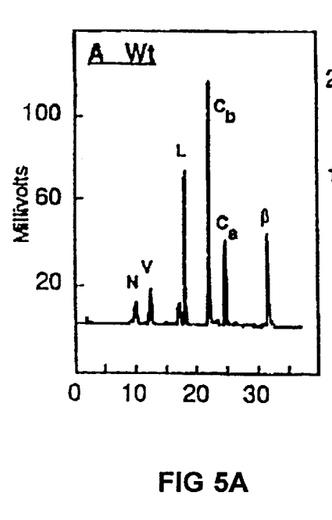
FIGS. 5A–5C present the results of C18 HPLC separation of lipid soluble pigments from wild-type plants on MS2 media, homozygous pds1 mutants on MS2 media supplemented with pOHPP, and homozygous pds1 mutants on MS2 media supplemented with homogentistic acid (HGA).
Figure 5B:
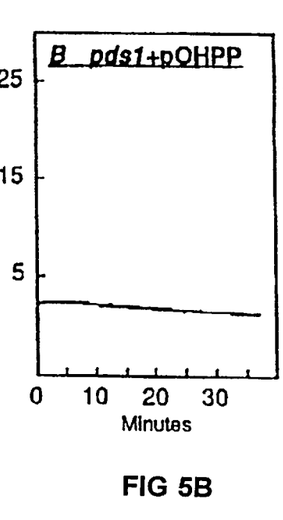
Figure 5C:
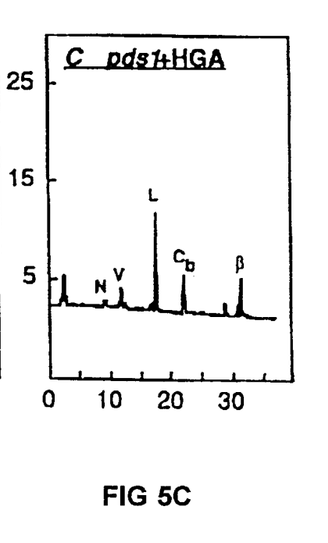
Figure 6A:
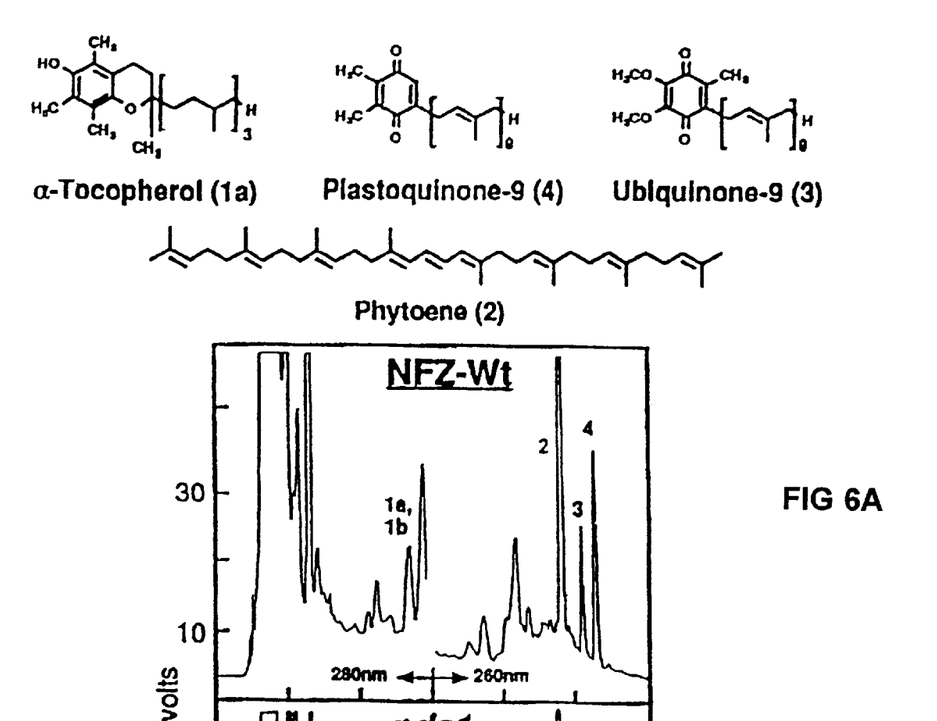
FIGS. 6A–6B present the results of C8 HPLC analyses of quinones in NFZ-wt and pds1 tissues.
Figure 6B:
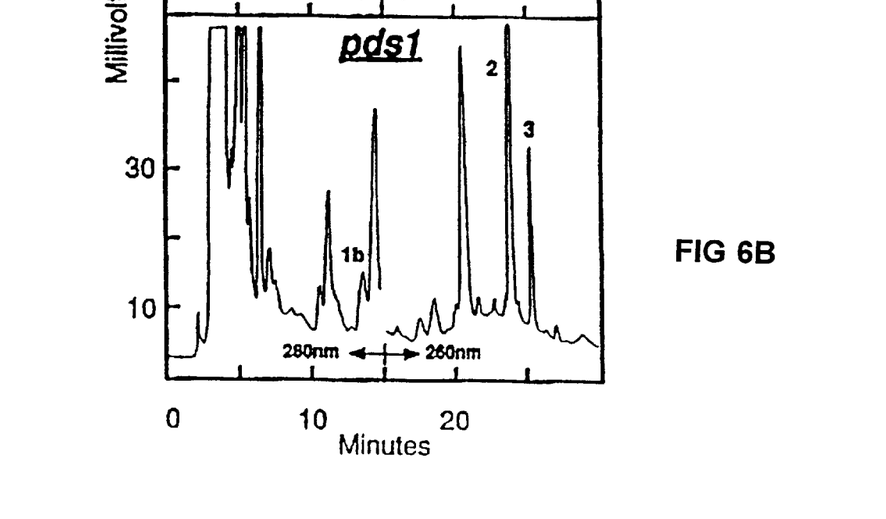

The present inventors demonstrated by biochemical complementation that the pds1 mutation affects the enzyme p-hydroxyphenyl pyruvic acid dioxygenase (pOHPP dioxygenase), because pds1 plants can be rescued by growth on the product but not the substrate of this enzyme, homogentisic acid (HGA) and p-hydroxyphenylpyruvate (pOHPP), respectively. pOHPP dioxygenase is the key branch point enzyme and committed step in the synthesis of both Vitamin E and plastoquinones and several independent lines of biochemical evidence confirm pds1 affects this enzyme (FIGS. 1, 5, 6). These results provide the first genetic evidence that plastoquinones are essential components for carotenoid synthesis in higher plants, most likely as an electron carrier/redox element in the desaturation reaction (FIG. 2). The Arabidopsis pOHPP dioxygenase gene/cDNA thus provides a basis for modifying the production of plastoquinones, α-tocopherol and carotenoids in all higher plants.

Specifically, the specification describes the genetic identification of the Arabidopsis pOHPP dioxygenase gene by mutational analysis, the physical isolation and functional confirmation of an Arabidopsis pOHPP dioxygenase cDNA, its nucleotide sequence and its use to isolate pOHPP dioxygenase genes and cDNAs from other plant species. Also included in the specification is a description of the use of the Arabidopsis pOHPP dioxygenase cDNA, and related cDNAs from other plants, to positively or negatively modify the expression/activity of pOHPP dioxygenase by recombinant techniques (overexpression, cosuppression, antisense, etc.) in any and all plant tissues, especially leaf and fruit tissues, to positively or negatively affect the production of α-toc, PQ and carotenoids.

Elevating pOHPP dioxygenase protein levels increases the amount of homogentisic acid (HGA) synthesized in plant tissues. Because HGA is the limiting precursor molecule for α-toc and PQ synthesis (the end products of the pathway), increasing HGA synthesis increases the levels of α-toc (Vitamin E) and PQ in plant tissues. The increase in PQ indirectly increases the synthesis of carotenoids, which require PQ for their synthesis. In addition, the increase in PQ increases photosynthetic efficiency by increasing electron flow between photosystem II and photosystem I, because PQ is the primary electron transporter between the two photosystems. The increase in α-toc, a well-studied antioxidant in mammals, increases the ability of plants to withstand oxidative stresses, such as that caused by high light, high temperature, water stress, ozone stress, UV stress or other abiotic or biotic stresses. Elevating the levels of pOHPP dioxygenase will modify the dose response curve of herbicides targeting pOHPP dioxygenase, thus increasing the relative resistance to such herbicides in transgenic plants as compared to native plants of the same species. Inhibiting the expression of pOHPP dioxygenase is expected to have the opposite effect.

Genetic Construct

To express pOHPP dioxygenase in a plant, it is required that a DNA sequence containing the pOHPP dioxygenase coding sequence be combined with regulatory sequences capable of expressing the coding sequence in a plant. A number of effective plant promoters, both constitutive and developmentally or tissue specific, are known to those of skill in the art. A transcriptional termination sequence (polyadenylation sequence) may also be added. Plant expression vectors, or plasmids constructed for expression of inserted coding sequences in plants, are widely used in the art to assemble chimeric plant expression constructs including the coding sequence, and to conveniently transfer the constructs into plants. A sequence which codes for pOHPP dioxygenase includes, for example, SEQ ID NO:1, or versions of the designated sequence sufficient to effect coding for the expression of pOHPP dioxygenase. Commonly used methods of molecular biology well-known to those of skill in the art may be used to manipulate the DNA sequences.

By "genetic construct" we mean any of a variety of ways of combining the protein-encoding sequences with a promoter sequence (and termination sequence, if necessary) in a manner that operably connects the promoter sequence (and termination sequence, if present) with the protein-encoding sequences. Typically, the promoter sequence will be "upstream" of a protein-encoding sequence, while the termination sequence, if used, will be "downstream" of the protein-encoding sequences.

The protein-encoding, promoter and termination sequences may be combined on a plasmid or viral vector, and inserted into a microbial host. Other functional sequences may be added to the gene construct. Alternatively, the protein-encoding, promoter, and termination sequence, if added, may be combined with any other needed functional sequences and used without a vector.

The DNA sequence described by SEQ ID NO:1 is sufficient to effect coding for the expression of pOHPP dioxygenase. However, it is envisioned that the above sequence could be truncated and still confer the same properties. It is not known at present which specific deletions would be successful, but it is likely that some deletions to the protein would still result in effective enzymatic activity. One skilled in the art of molecular biology would be able to take the designated sequence and perform deletional analysis experiments to determine what portions of the designated sequence are essential to effect coding for the expression of pOHPP dioxygenase. One could create a genetic construct with the candidate deletion mutations and perform experiments as described below in the Examples, to test whether such deletion mutation sequences effect coding for the enzyme. Expression of the enzyme activity indicates a successful deletion mutant or mutants. In this manner, one could determine which parts of the designated sequence is essential for expression of the enzyme.

It is also known that the genetic code is degenerate, meaning that more than one codon, or set of three nucleotides, codes for each amino acid. Thus it is possible to alter the DNA coding sequence to a protein, such as the sequence for pOHPP dioxygenase described here, without altering the sequence of the protein produced. Selection of codon usage may affect expression level in a particular host. Such changes in codon usage are also contemplated here.

It is further contemplated that using the Arabidopsis pOHPP gene coding sequence described here, that the homologous pOHPP dioxygenase sequences from other higher plants can be readily recovered. Oligonucleotides can be made from the sequence set forth below to either hybridize against cDNA or genomic libraries or used for PCR amplification of homologous pOHPP dioxygenase sequences from other plants.

Once a pOHPP gene is in hand, whether from Arabidopsis or from some other plant species, it then becomes possible to insert a chimeric plant expression genetic construct into any plant species of interest. Suitable plant transformation methods exist to insert such genetic constructs into most, if not all, commercially important plant species. Presently known methods include Agrobacterium-mediated transformation, coated-particle gene delivery (Biolistics) and electroporation, in which an electric voltage is used to facilitate gene insertion. All these methods, and others, can insert the genetic construct into the genome of the resulting transgenic plant in such a way that the genetic construct becomes an inheritable trait, transmitted to progeny of the original transgenic plant by the normal rules of Mendelian inheritance. Thus, once a genetic construct expressing a pOHPP gene is inserted into a plant, it can become a part of a plant breeding program for transfer into any desired genetic background.

To over-express pOHPP dioxygenase, a genetic construct may be used with a higher strength promoter. To inhibit expression of endogenous pOHPP dioxygenase, an antisense genetic construct can be made, as is known by those of skill in the art, to reduce the level of pOHPP dioxygenase present in the plant tissues.

EXAMPLES

Isolation of pds1, a Mutant Defective in Carotenoid Synthesis

To further understand carotenoid biosynthesis and its integration with other pathways in the chloroplast in higher plants, the present inventors studied the pathway by isolating Arabidopsis thaliana mutants that are blocked in carotenoid synthesis.

Plants homozygous for defects in the early stages of carotenoid synthesis (e.g. prior to production of β-carotene) are lethal when grown in soil and the isolation of such mutations requires the design of screening procedures to identify plants heterozygous for soil lethal mutations. The present inventors found that most soil lethal, homozygous pigment-deficient Arabidopsis mutants can be grown to near maturity in tissue culture on Murashige and Skoog basal media (Murashige and Skoog, Physiol. Plant. 15:473–497, 1962) supplemented with sucrose (MS2 media). Under these conditions, photosynthesis and chloroplast development are essentially dispensable and all the energy and nutritional needs of the plant are supplied by the media.

Greater than 500 lines from the 10,000 member Feldmann T-DNA tagged Arabidopsis thaliana population (Forsthoefel et al., Aust. J. Plant Physiol. 19:353–366, 1992) were selected for pigment analysis based on their segregation for lethal pigment mutations. Seed from plants heterozygous for lethal pigment mutations were surface sterilized, grown on MS2 media, the segregating pigment mutants identified, tissue harvested from individual plants, and HPLC pigment analysis performed. Although numerous mutant lines with severe pigment deficiencies were identified, only two were found to be carotenoid biosynthetic mutants. One mutant line isolated from this group, pds1, is described in detail here.

The hallmark phenotype for disruption of a biosynthetic pathway is the accumulation of an intermediate compound prior to the site of blockage. Such blockage of the carotenoid pathway can be mimicked chemically by treatment of wild-type plants with the herbicide NFZ, an inhibitor of the phytoene desaturase enzyme (FIG. 1) which has been reported to cause accumulation of phytoene in treated tissues. Britton, Z. Naturforsch 34c:979–985, 1979. FIGS. 3A–3E present the results of pigment analysis of wild-type, NFZ-wt, and pds1 tissues. Abbreviations in FIGS. 3A–3E are as follows: N, neoxanthin; V, violaxanthin; L, lutein; Cb, chlorophyll b; Ca, chlorophyll a; β, β-carotene.

Figure 3A:
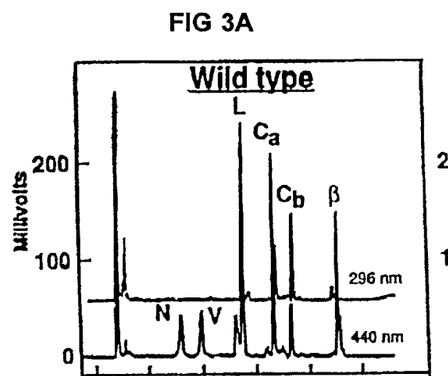
FIGS. 3A–3E are graphs of pigment analyses of wild-type, NFZ-wt, and pds1 tissues.
Figure 3B:
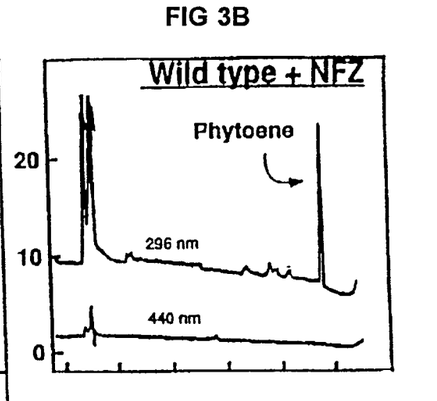
Figure 3C:
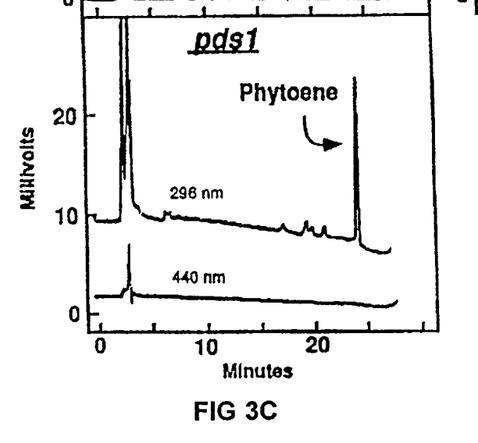
Figure 3D:
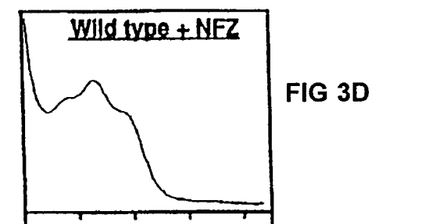
Figure 3E:
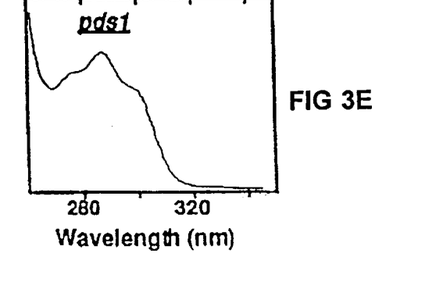

FIG. 3A shows $C_{18}$, Reverse Phase HPLC analysis of the carotenoids that accumulate in wild-type Arabidopsis thaliana leaves. In comparison, FIG. 3B shows the pigment profile for NFZ treated wild-type (NFZ-Wt). Spectral analysis of the strongly absorbing 296 nm peak at 33 minutes in NFZ-Wt tissue shows absorbance maxima at 276, 286, and 298 nm, indicative of phytoene (FIG. 3D). FIG. 3C shows pigment analysis of tissue culture grown homozygous pds1 mutant plants. The low absorbance at 440 nm in FIGS. 3B and C demonstrates that like NFZ-Wt, pds1 mutants lack all chlorophylls and carotenoids that normally accumulate in wild-type tissue (compare to FIG. 3A). However, unlike wild-type, pds1 mutants contain a peak with a retention time at approximately 33 minutes that absorbs strongly at 296 nm. The retention time and absorbance of the 33-minute peak in the pds1 mutant corresponds to the phytoene peak in pigment extracts of NFZ-Wt tissue (FIG. 3B). Spectral analysis of the 33-minute peak from pds1 is shown in FIG. 3E and is virtually identical to the spectra of phytoene from NFZ-Wt tissue (FIG. 3D) as well as to the published spectra for phytoene. These results confirm the chemical identity of the accumulating compound in pds1 as phytoene and conclusively demonstrate that the pds1 mutation disrupts carotenoid biosynthesis.

Carotenoid Analysis

For quantitative and qualitative carotenoid analysis, plant tissue is placed in a microfuge tube and ground with a micropestle in 200 μl of 80% acetone. 120 μl of ethyl acetate is added and the mixture vortexed. 140 μl of water is added and the mixture centrifuged for 5 minutes. The carotenoid containing upper phase is then transferred to a fresh tube and vacuum dried in a Jouan RC1010 Centrifugal Evaporator. The dried extract is resuspended in ethyl acetate at a concentration of 0.5 mg fresh weight of tissue per μl and either analyzed immediately by HPLC or stored at -80° C. under nitrogen.

Carotenoids were separated by reverse-phase HPLC analysis on a Spherisorb ODS2 5 micron $C_{18}$ column, 25 cm in length (Phase Separations Limited, Norwalk, Conn.) using a 45 minute gradient of Ethyl Acetate (0–100%) in Acetonitrile/water/triethylamine (9:1:0.01 v/v), at a flow rate of 1 ml per minute (Goodwin and Britton, 1988). Carotenoids were identified by retention time relative to known standards with detection at both 296 nm and 440 nm. When needed, absorption spectra for individual peaks were obtained with a Hewlett Packard 1040A photodiode array detector and compared with published spectra or available standards.

Quinone Analysis

Quinones were extracted from tissue using a method modified from that described in Bligh et al., *Can. J. Biochem. Physiol.* 37:911–917, 1959. Frozen plant tissue was ground in a mortar with 3 volumes of chloroform and 6 volumes of methanol and transferred to a test tube. Water and additional chloroform were added until a biphasic mixture was obtained. The quinone containing chloroform phase was then collected. To increase yields, the aqueous phase was back—extracted with chloroform, the two chloroform phases pooled, and then filtered through Whatman #3 filter paper. The resulting filtrate was dried under a constant stream of nitrogen. Once dried, the pellet was resuspended in methanol at a concentration of 10 mg fresh weight per ml and immediately analyzed by HPLC. Quinones were resolved by reversed-phase HPLC analysis on a LiChrosorb RP-8, 5 micron column, 25 cm in length, (Alltech, San Jose, Calif.) using an isocratic solvent of 10% $H_2O$ in Methanol for the first 14 minutes, at which time the solvent was switched to 100% methanol for the remainder of the run (modified from the method described in Lichtenthaler, *Handbook of Chromatography*, CRC Press, 115–159, 1984). The flow rate was 1 ml per minute for the duration. Peaks were identified based upon the retention time of known standards with detection at 280 nm for α-tocopherol and 260 nm for plastoquinone and ubiquinone as well as by absorption spectra from a Hewlett Packard 1040A photodiode array detector. When needed, fractions represented by individual chromatographic peaks were collected, and submitted to the Southwest Environmental Health Science Center, Analytical Core laboratory for mass spectral analysis. Results were obtained using a TSQ7000 tandem mass spectrometer (Finnigan Corp., San Jose, Calif.) equipped with an atmospheric pressure chemical ionization source operated in the positive ion mode. The instrument was set to unit resolution and the samples were introduced into the source in a 0.3 ml/minute methanol stream and ionized using a 5 kV discharge.

Genetic Analysis of pds1

The genetic nature of the pds1 mutation was determined by analyzing seeds resulting from selfing pds1 heterozygous plants. Prior to desiccation, F1 seeds were scored as either green (wild-type or heterozygous) or white (homozygous). A 3:1 segregation ratio was observed (146 green seeds: 48 white seeds), indicating that pds1 is inherited as single recessive nuclear mutations ($X^2$=0.01, p>0.90). Because pds1 mutants are inhibited in the desaturation of phytoene, the inventors believed that it might be a mutation in the phytoene desaturase enzyme, which had previously been mapped to chromosome 4, between ag and bp. Wetzel et al., *Plant J.* 6:161–175, 1994. To test this hypothesis, the pds1 mutation was mapped relative to visible markers. The pds1 mutation was found to map to chromosome 1, approximately 7 cM from dis1 toward clv2. Franzmann et al., *Plant J.* 7:341–350, 1995. These data points are summarized in FIG. 4 and establish that pds1 does not map to the phytoene desaturase enzyme locus, thus proving that the pds1 mutation is not in the phytoene desaturase enzyme. This data provided important insight for characterization of the pds1 mutant.

Homozygous pds1 Mutants can be Rescued by Homogentisic Acid, an Intermediate in Plastoquinone and Tocopherol Biosynthesis As described earlier, previous research suggesting a role for quinones and pOHPP dioxygenase in phytoene desaturation lead the present inventors to investigate the quinone biosynthetic pathway in the pds1 mutant. The early stages of plastoquinone/tocopherol synthesis were functionally analyzed by growth in the presence of two intermediate compounds in the pathway, p-hydroxyphenylpyruvate (pOHPP) and homogentisic acid (HGA) (refer to FIGS. 1 and 2). Albino pds1 homozygous plants were first germinated on MS2 media and then transferred to MS2 media supplemented with 100 μM of either pOHPP or HGA. pds1 plants remained albino when transferred to media containing pOHPP but greening occurred when pds1 plants were transferred to media containing HGA. FIGS. 5A–5C present the results of complementation of the pds1 mutation with homogentisic acid. Each profile represents pigments extracted from 10 mg fresh weight of tissue. Abbreviations used in FIGS. 5A–5C are as described in FIGS. 3A–3E. HPLC analysis with detection at 440 nm of the carotenoids extracted from pds1 plants grown on pOHPP and HGA are shown in FIGS. 5B and C, respectively. The pigment profiles of pds1 mutants grown on pOHPP are similar to the profiles of pds1 plants grown on MS2 media shown in FIG. 3B. Comparison of the pigment profiles for pds1+HGA tissue and wild-type tissue (FIGS. 5A and 5C) indicates that growth in the presence of HGA is able to qualitatively restore a wild-type carotenoid profile to albino, homozygous pds1 plants. These results indicate that the pds1 mutation affects the enzyme pOHPP dioxygenase, because pds1 mutants are not altered by growth on the substrate of this enzyme, pOHPP, but rather, are restored qualitatively to wild-type pigmentation by growth on the product of this enzyme, HGA (refer to FIGS. 1 and 2). The complementation of pds1 with HGA also indicates that intermediates or end products of this pathway (plastoquinone and/or tocopherols, refer to FIGS. 1 and 2) are necessary components for phytoene desaturation in plants and confirms the observation of Schultz et al. in FEBS where inhibitors of pOHPP dioxygenase were shown to cause accumulation of phytoene.

HPLC Analysis Conclusively Demonstrates that pds1 is a Mutation in the Plastoquinone/Tocopherol Biosynthetic Pathway that also Affects Carotenoid Synthesis In addition to biochemical complementation of pds1 mutants, the plastoquinone/tocopherol pathway was also directly analyzed in pds1 tissue by utilizing $C_8$ HPLC to resolve total lipid extracts and identify three separate classes of quinones: ubiquinone, plastoquinone, and α-tocopherol (Vitamin E) (FIGS. 5 and 6). Ubiquinone and plastoquinone perform analogous electron transport functions in the mitochondria and chloroplast, respectively, but are synthesized by different pathways in separate subcellular compartments (Goodwin et al., *Introduction to Plant Biochemistry*, Oxford, Pergamon Press, 1983), making ubiquinone an ideal internal control in these analyses. FIG. 6 shows the $C_8$ HPLC analysis of lipid soluble extracts from NFZ-Wt tissue and pds1 tissue. In NFZ-Wt tissue (FIG. 6A), peaks 3 and 4 were identified as ubiquinone and plastoquinone, respectively, based on retention time (26 and 27 minutes), optical spectra, and mass spectra (results not shown). NFZ-Wt tissue contained a peak (1) with a retention time of 13.5 minutes which was identified as α-tocopherol based upon the retention time of a standard. However, optical spectroscopy and mass spectrometry demonstrated that peak 1 was composed of two major components: α-tocopherol (1a) and an unidentified compound (1b). The mass of α-tocopherol was determined to be 430 as indicated by the presence of the 431 protonated molecule while the molecular mass of the unidentified compound was 412, as indicated by the presence of the 413 protonated molecule (data not shown), clearly demonstrating the presence of two compound in peak 1. This quinone analysis demonstrates that the herbicide NFZ, which specifically inhibits the phytoene desaturase enzyme, does not affect synthesis of homogentisate derived quinones. pds1 tissue (FIG. 6B) contain ubiquinone (peak 3) but lack plastoquinone (peak 4). Additionally, though pds1 contains a peak at 13.5 minutes, optical spectroscopy and mass spectrometry data demonstrate that this peak lacks α-tocopherol (1a) and is composed solely of the compound 1b (data not shown). Therefore, homozygous pds1 plants accumulate ubiquinone but lack both plastoquinone and α-tocopherol. This is consistent with the pds1 mutation affecting pOHPP dioxygenase (refer to FIGS. 1 and 2), as suggested by the rescue of the mutation by HGA, and provide additional evidence that the pds1 mutation disrupts pOHPP dioxygenase.

Isolation of a Truncated, Putative pOHPP Dioxygenase Arabidopsis cDNA

The observation of Schultz et al. demonstrating that inhibitors of pOHPP dioxygenase activity disrupt carotenoid synthesis and cause accumulation of phytoene provided important insight for the characterization of the pds1 mutant which in turn provided the present inventors with important insight for the isolation of a putative cDNA for the pds1 locus. In animals, genetic defects which inhibit the activity of pOHPP dioxygenase lead to tyrosinemia type I, a fatal inherited disease in aromatic amino acid catabolism characterized by the presence of high levels of pOHPP in the urine.

In an effort to further understand the nature of this disease, pOHPP dioxygenase cDNAs have been cloned from several mammalian and bacterial sources (summarized in Ruetschi et al., *Eur. J. Biochem.* 205:459–466, 1992). Amino acid identity between various mammalian pOHPP dioxygenase enzymes is >80%; in comparison, their identity to bacterial homologs is very low, less than 28%. By using mammalian and bacterial sequences to search the Expressed Sequence Tags (ESTs) computer DNA database (Newman et al., *Plant Physiol.* 106:1241–1255, 1994), one partial length Arabidopsis EST was identified and used as a probe. The partial length Arabidopsis probe corresponds to base pairs 1072 through 1500 of SEQ ID NO:1.

This cDNA contained only 99 amino acids of the carboxyl terminal portion of the protein coding region. The deduced protein sequence of this putative Arabidopsis pOHPP dioxygenase cDNA shows similar homology (~50% identity) to both the mammalian and bacterial pOHPP dioxygenases. Interestingly, the partial Arabidopsis sequence also contains a 15 amino acid insertion not found in the human or bacterial enzymes. Finally, alignment of six pOHPP dioxygenase sequences from mammals and bacteria identified three regions of high conservation, the highest being a 16 amino acid region near the carboxy end of pOHPP dioxygenases that shows 62.5% identity across all phyla. Ruetschi et al., *Eur. J. Biochem.* 205:459–466, 1992. This region is also present in the truncated Arabidopsis sequence. The lines of evidence suggest that the partial length Arabidopsis cDNA described above encodes a pOHPP dioxygenase, most likely the pds1 locus.

Isolation and Characterization of a Full Length ArabidopsispOHPP Dioxygenase cDNA Utilizing the partial length Arabidopsis cDNA probe, an Arabidopsis cDNA library was screened by nucleic acid hybridization for full length cDNAs. A large number of hybridizing cDNAs were isolated, and one of the longest, pHPP1.5, containing a 1,520 bp insertion, was sequenced completely; the insert is presented as SEQ ID NO:1. pHPP1.5 encodes a 446 amino acid protein (presented as SEQ ID NO:2), which is slightly larger in size than mammalian and bacterial pOHPP dioxygenases. pHPP1.5 shows 34–40% identity at the amino acid level to pOHPP dioxygenases from various mammals and bacteria. In comparing four bacterial pOHPP dioxygenases and one mammalian pOHPP dioxygenases (pig) which ranged in size from 346–404 amino acids, Denoya et al. identified 69 amino acids that were conserved between all five pOHPP dioxygenases. Denoya et al., *J. Bacteriol.* 176:5312–5319, 1994. The pHPP1.5 coding region contains 52 of these 69 conserved amino acids.

Demonstration that pHPP1.5 Encodes an Active pOHPP Dioxygenase Protein and Complements the pds1 Mutation In order to definitively demonstrate that pHPP1.5 is the gene product encoded by the pds1 locus and that it encodes a functional pOHPP dioxygenase protein, the pHPP1.5 cDNA was cloned into a plant transformation vector for molecular complementation experiments with the pds1. The full length wild-type pOHPP dioxygenase cDNA will be subcloned into a plant transformation vector driven by the Cauliflower Mosaic Virus 35S (CaMV) promoter and containing all necessary termination cassettes and selectable markers (Kan$^r$). The CaMV promoter is a strong constitutive promoter. This single construct and the vector without the pHPP1.5 insert (as a control) will be used in vacuum infiltration transformation which uses whole soil grown plants and will be done on plants that are heterozygous for the pds1 mutation. Bouchez et al., CR Acad. Sci. Paris, *Sciences de la vie* 316, 1993.

In the standard procedure, 20–30 soil grown plants will be independently transformed and analyzed separately. In this case homozygous plants containing the pds1 mutation would be lethal while heterozygous plants containing the pds1 mutation would be segregating 2:1 for the pds1 mutation in their siliques. The inventors will use a similar number of wild type plants in a parallel transformation as a control.

After transformation of the pds1 segregating plant population, as the plants are setting seed the inventors can easily identify those heterozygous for the pds1 mutation in retrospect by inspection of their siliques which would contain green:white embryos in a 3:1 ratio.

Figure 4:
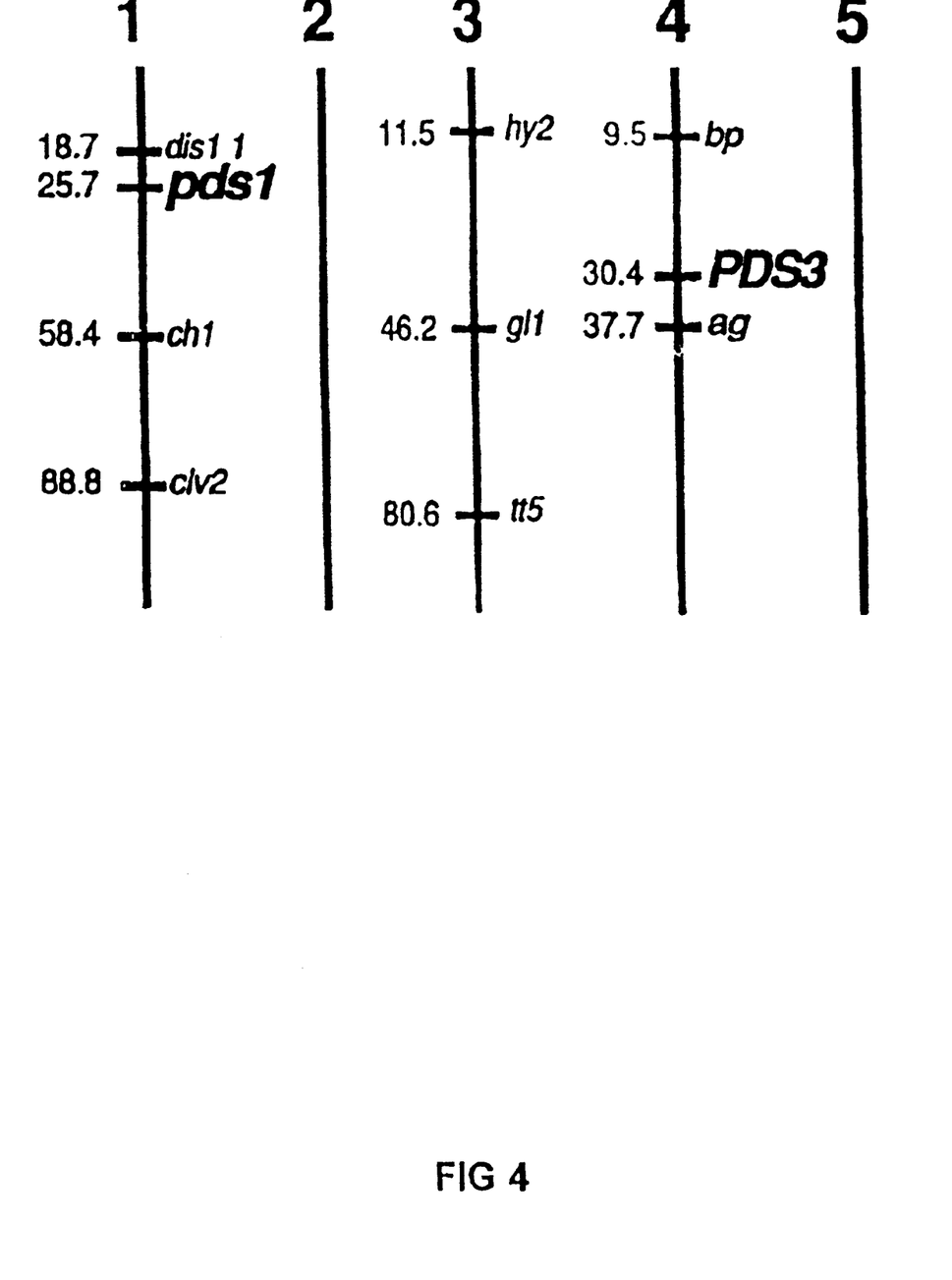
FIG. 4 is a physical map of the pds1 mutation relative to visible markers.

Seed harvested from individually transformed heterozygous pds1 plants will be germinated on kanamycin and resistant seedlings transferred to soil. Segregation analysis of seed from these primary transformants (T2 seed) and T3 seed for segregation of the pds1 phenotype (albino and phytoene accumulating) and the T-DNA encoded kanamycin resistance marker (wild type pOHPP dioxygenase cDNA) will conclusively demonstrate complementation of the pds1 mutation with the pOHPP dioxygenase cDNA. To provide additional proof that pHPP1.5 is encoded by the pds1 locus, the pHPP1.5 cDNA has been mapped relative to the pds1 locus using recombinant inbred lines, as described in Lister et al., Plant J. 4:745–750, 1993. The pHPP1.5 cDNA mapped to the region of chromosome 1 containing the pds1 mutation (FIG. 4). Finally, the pHPP1.5 cDNA will be overexpressed in E. coli and the activity of the protein determined.

Modification of pOHPP Expression

From the genetic and biochemical studies described above it is clear that only one pOHPP dioxygenase gene product is involved in chloroplastic quinone synthesis, that the pds1 mutation defines this gene, that the pHPP1.5 cDNA is the product encoded by the pds1 locus and that disruption of its function completely eliminates Vitamin E production and plastoquinone and carotenoid synthesis in plant tissues. Modification of pOHPP dioxygenase expression in plants by molecular techniques using pHPP1.5 can therefore be used to positively or negatively affect the production of tocopherols, plastoquinones directly and carotenoids indirectly (refer to FIGS. 1 and 2). Specifically, overexpression of the pOHPP dioxygenase enzyme will result in increased levels of one or more of these compounds in the tissues of transgenic plants. Alternatively, using antisense techniques, it is possible to lower the level of enzyme activity to decrease the levels of these compounds in plants. Additionally, overexpression of the pOHPP dioxygenase will enable a transgenic plant to withstand elevated levels of herbicides that target this enzyme, providing agrinomically significant herbicide resistance relative to normal plants.

Two different plant systems, Arabidopsis and tomato, are being used to demonstrate the effects of modified pOHPP dioxygenase in plant tissues. Constitutive overexpression of pOHPP dioxygenase will be done in both plant systems utilizing the CaMV 35S promoter and the pHPP1.5 cDNA. The consequences of this altered expression on tocopherol, plastoquinone and carotenoid levels and profiles in various plant tissues will be determined as described below. In tomato, tissue specific overexpression of pOHPP dioxygenase (pHPP1.5) will be driven by the fruit specific promoter derived from the tomato βsubunit gene, which is expressed specifically in developing, but not ripening tomato fruit. This will determine the potential for modifying the levels of tocopherol, plastoquinone and carotenoids specifically in developing and ripening fruit for nutritional purposes without affecting their production in other plant tissues. These combined experiments will determine whether pOHPP dioxygenase is a rate limiting step in chloroplastic homogentisic acid derived quinone synthesis and the potential for manipulating chloroplastic homogentisic acid derived quinones (tocopherols and plastoquinones) and compounds that require quinones for their synthesis (carotenoids, etc) by increasing pOHPP dioxygenase activity.

Multiple independent transformants will be produced for each construct and plant species used. The integration and gene copy number of each chimeric gene in each line will be confirmed by southern analysis, the level of pOHPP mRNA determined by Northern blot analysis, pOHPP dioxygenase activity determined as described in Schulz et al., FEBS 318:162–166, 1993, and the effects on individual chloroplastic components of interest analyzed (tocopherols, plastoquinones and carotenoids). In green tissue containing constitutively expressing constructs this analysis can occur relatively soon after transformants are put into soil. Analysis of fruit specific construct lines will require much more time for fruit set to occur. Analysis of tocopherols, plastoquinones and carotenoids will be by a combination of HPLC, optical and mass spectra as described in Norris et al. (1995, in press). Analysis of tocopherol levels is performed by HPLC and when needed by GC:mass spectroscopy in selected ion mode. In MS analysis the absolute level of tocopherol will be quantified by isotopic dilution with a known, "heavy carbon" tocopherol standard added at the start of the extraction. Determination based on fresh weight of tissue can also be performed. Plastoquinone levels will be quantified by C8 HPLC and optical spectra as described in Norris et al. (1995, in press). Total carotenoid levels are determined spectrophotometrically and the levels of individual carotenes quantified by C18 HPLC and optical spectra quantified to standards. In the course of these experiments we will identify high expressing lines with simple insertions that segregate as single genetic loci in progeny. This will facilitate analysis of the inheritance of the gene and phenotype in future generations.

Overexpression of pOHPP for in vitro Herbicide Analysis pOHPP dioxygenase will be overexpressed in E. coli or other prokaryotic or eukaryotic protein production systems and purified in large amounts for use in enzymatic assays for identifying new herbicide compounds (pOHPP inhibitors) and optimizing existing chemistries through detailed kinetic analysis.

We claim:

1. An isolated DNA encoding an Arabidopsis p-hydroxyphenyl pyruvic acid dioxygenase.

2. The DNA of claim 1 wherein the DNA is SEQ ID NO:1.

3. An expression vector operable in plants comprising the DNA of claim 1.

4. A DNA plant gene expression construct comprising in operable linkage:
   a) a promoter effective in plant cells;
   b) a DNA encoding an Arabidopsis p-hydroxyphenyl pyruvic acid dioxygenase; and
   c) a 3' termination sequence effective in plant cells.

5. A DNA construct comprising:
   a) a promoter capable of expressing a downstream coding sequence in a tomato plant;
   b) a DNA encoding an Arabidopsis p-hydroxyphenyl pyruvic acid dioxygenase; and
   c) a 3' termination sequence, wherein the construct expresses the DNA when transformed into tomato plants.

6. A microbial host transformed with the vector of claim 3.

7. A bacterium transformed with the DNA construct of claim 5.

8. A tomato plant cell transformed with the DNA construct of claim 5.

9. A transgenic tomato plant transformed with a DNA construct comprising the DNA of claim 1.

10. A transgenic Arabidopsis plant transformed with a DNA construct comprising the DNA of claim 1.

11. A transgenic tomato plant comprising in its genome a DNA construct comprising, 5' to 3':
    a) a promoter effective in tomato;
    b) a DNA coding region encoding an Arabidopsis p-hydroxyphenyl pyruvic acid dioxygenase; and
    c) a transcriptional terminator,
       wherein the DNA construct expresses the DNA coding region in the tomato plant.

12. A transgenic tomato plant comprising in its genome a DNA construct comprising, 5' to 3':
    a) a promoter effective in tomato;
    b) a DNA coding region encoding p-hydroxyphenyl pyruvic acid dioxygenase; and
    c) a transcriptional terminator, wherein the DNA construct expresses the DNA coding region in the tomato plant, ad wherein the DNA coding region is that set forth in SEQ ID NO:1.

13. A transgenic plant comprising in its genome a DNA construct comprising, 5' to 3':
    a) a promoter effective in plant cells;
    b) the DNA sequence of SEQ ID NO:1; and
    c) a transcriptional terminator,
       wherein the DNA construct expresses p-hydroxyphenyl pyruvic acid dioxygenase in cells of the plant.

14. Seed of the tomato plant of claim 11.

15. Fruit of the tomato plant of claim 11.

16. A method of producing a transgenic plant comprising introducing into the genome of a plant a DNA construct comprising 5' to 3':
    a) a promoter effective in plant cells; and
    b) a DNA encoding an Arabidopsis p-hydroxyphenyl pyruvic acid dioxygenase.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1519 base pairs -continued

```
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Arabidopsis thaliana (vii) IMMEDIATE SOURCE:
        (B) CLONE: pHPP1.5

(ix) FEATURE:
        (A) NAME/KEY: CDS
        (B) LOCATION: 37..1374

(xi) SEQUENCE DESCRIPTION: SEQ ID NO:1:

CCACGCGTCC GAGTTTTAGC AGAGTTGGTG AAATCA ATG GGC CAC CAA AAC GCC       54
                                        Met Gly His Gln Asn Ala
                                         1               5

GCC GTT TCA GAG AAT CAA AAC CAT GAT GAC GGC GCT GCG TCG TCG CCG      102
Ala Val Ser Glu Asn Gln Asn His Asp Asp Gly Ala Ala Ser Ser Pro
             10                  15                  20

GGA TTC AAG CTC GTC GGA TTT TCC AAG TTC GTA AGA AAG AAT CCA AAG      150
Gly Phe Lys Leu Val Gly Phe Ser Lys Phe Val Arg Lys Asn Pro Lys
         25                  30                  35

TCT GAT AAA TTC AAG GTT AAG CGC TTC CAT CAC ATC GAG TTC TGG TGC      198
Ser Asp Lys Phe Lys Val Lys Arg Phe His His Ile Glu Phe Trp Cys
 40                  45                  50

GGC GAC GCA ACC AAC GTC GCT CGT CGC TTC TCC TGG GGT CTG GGG ATG      246
Gly Asp Ala Thr Asn Val Ala Arg Arg Phe Ser Trp Gly Leu Gly Met
 55                  60                  65                  70

AGA TTC TCC GCC AAA TCC GAT CTT TCC ACC GGA AAC ATG GTT CAC GCC      294
Arg Phe Ser Ala Lys Ser Asp Leu Ser Thr Gly Asn Met Val His Ala
             75                  80                  85

TCT TAC CTA CTC ACC TCC GGT GAC CTC CGA TTC CTT TTC ACT GCT CCT      342
Ser Tyr Leu Leu Thr Ser Gly Asp Leu Arg Phe Leu Phe Thr Ala Pro
         90                  95                 100

TAC TCT CCG TCT CTC TCC GCC GGA GAG ATT AAA CCG ACA ACC ACA GCT      390
Tyr Ser Pro Ser Leu Ser Ala Gly Glu Ile Lys Pro Thr Thr Thr Ala
        105                 110                 115

TCT ATC CCA AGT TTC GAT CAC GGC TCT TGT CGT TCC TTC TTC TCT TCA      438
Ser Ile Pro Ser Phe Asp His Gly Ser Cys Arg Ser Phe Phe Ser Ser
120                 125                 130

CAT GGT CTC GGT GTT AGA GCC GTT GCG ATT GAA GTA GAA GAC GCA GAG      486
His Gly Leu Gly Val Arg Ala Val Ala Ile Glu Val Glu Asp Ala Glu
135                 140                 145                 150

TCA GCT TTC TCC ATC AGT GTA GCT AAT GGC GCT ATT CCT TCG TCG CCT      534
Ser Ala Phe Ser Ile Ser Val Ala Asn Gly Ala Ile Pro Ser Ser Pro
                155                 160                 165

CCT ATC GTC CTC AAT GAA GCA GTT ACG ATC GCT GAG GTT AAA CTA TAC      582
Pro Ile Val Leu Asn Glu Ala Val Thr Ile Ala Glu Val Lys Leu Tyr
            170                 175                 180

GGC GAT GTT GTT CTC CGA TAT GTT AGT TAC AAA GCA GAA GAT ACC GAA      630
Gly Asp Val Val Leu Arg Tyr Val Ser Tyr Lys Ala Glu Asp Thr Glu
        185                 190                 195

AAA TCC GAA TTC TTG CCA GGG TTC GAG CGT GTA GAG GAT GCG TCG TCG      678
Lys Ser Glu Phe Leu Pro Gly Phe Glu Arg Val Glu Asp Ala Ser Ser
200                 205                 210

TTC CCA TTG GAT TAT GGT ATC CGG CGG CTT GAC CAC GCC GTG GGA AAC      726
Phe Pro Leu Asp Tyr Gly Ile Arg Arg Leu Asp His Ala Val Gly Asn
215                 220                 225                 230

GTT CCT GAG CTT GGT CCG GCT TTA ACT TAT GTA GCG GGG TTC ACT GGT      774
```

-continued

```
Val Pro Glu Leu Gly Pro Ala Leu Thr Tyr Val Ala Gly Phe Thr Gly
                235                 240                 245

TTT CAC CAA TTC GCA GAG TTC ACA GCA GAC GAC GTT GGA ACC GCC GAG      822
Phe His Gln Phe Ala Glu Phe Thr Ala Asp Asp Val Gly Thr Ala Glu
            250                 255                 260

AGC GGT TTA AAT TCA GCG GTC CTG GCT AGC AAT GAT GAA ATG GTT CTT      870
Ser Gly Leu Asn Ser Ala Val Leu Ala Ser Asn Asp Glu Met Val Leu
                265                 270                 275

CTA CCG ATT AAC GAG CCA GTG CAC GGA ACA AAG AGG AAG AGT CAG ATT      918
Leu Pro Ile Asn Glu Pro Val His Gly Thr Lys Arg Lys Ser Gln Ile
            280                 285                 290

CAG ACG TAT TTG GAA CAT AAC GAA GGC GCA GGG CTA CAA CAT CTG GCT      966
Gln Thr Tyr Leu Glu His Asn Glu Gly Ala Gly Leu Gln His Leu Ala
295                 300                 305                 310

CTG ATG AGT GAA GAC ATA TTC AGG ACC CTG AGA GAG ATG AGG AAG AGG     1014
Leu Met Ser Glu Asp Ile Phe Arg Thr Leu Arg Glu Met Arg Lys Arg
                315                 320                 325

AGC AGT ATT GGA GGA TTC GAC TTC ATG CCT TCT CCT CCG CCT ACT TAC     1062
Ser Ser Ile Gly Gly Phe Asp Phe Met Pro Ser Pro Pro Pro Thr Tyr
                330                 335                 340

TAC CAG AAT CTC AAG AAA CGG GTC GGC GAC GTG CTC AGC GAT GAT CAG     1110
Tyr Gln Asn Leu Lys Lys Arg Val Gly Asp Val Leu Ser Asp Asp Gln
            345                 350                 355

ATC AAG GAG TGT GAG GAA TTA GGG ATT CTT GTA GAC AGA GAT GAT CAA     1158
Ile Lys Glu Cys Glu Glu Leu Gly Ile Leu Val Asp Arg Asp Asp Gln
360                 365                 370

GGG ACG TTG CTT CAA ATC TTC ACA AAA CCA CTA GGT GAC AGG CCG ACG     1206
Gly Thr Leu Leu Gln Ile Phe Thr Lys Pro Leu Gly Asp Arg Pro Thr
375                 380                 385                 390

ATA TTT ATA GAG ATA ATC CAG AGA GTA GGA TGC ATG ATG AAA GAT GAG     1254
Ile Phe Ile Glu Ile Ile Gln Arg Val Gly Cys Met Met Lys Asp Glu
                395                 400                 405

GAA GGG AAG GCT TAC CAG AGT GGA GGA TGT GGT GGT TTT GGC AAA GGC     1302
Glu Gly Lys Ala Tyr Gln Ser Gly Gly Cys Gly Gly Phe Gly Lys Gly
                410                 415                 420

AAT TTC TCT GAG CTC TTC AAG TCC ATT GAA GAA TAC GAA AAG ACT CTT     1350
Asn Phe Ser Glu Leu Phe Lys Ser Ile Glu Glu Tyr Glu Lys Thr Leu
                425                 430                 435

GAA GCC AAA CAG TTA GTG GGA TGA ACAAGAAGAA GAACCAACTA AAGGATTGTG    1404
Glu Ala Lys Gln Leu Val Gly *
440                 445

TAATTAATGT AAAACTGTTT TATCTTATCA AAACAATGTT ATACAACATC TCATTTAAAA   1464

ACGAGATCAA TCAAAAAATA CAATCTTAAA TTCAAAACCA AAAAAAAAAA AAAAA        1519

(2) INFORMATION FOR SEQ ID NO:2:

(i) SEQUENCE CHARACTERISTICS:
        (A) LENGTH:  445 amino acids
        (B) TYPE: amino acid
        (D) TOPOLOGY: linear (ii) MOLECULE TYPE: protein (xi) SEQUENCE DESCRIPTION: SEQ ID NO:2:

Met Gly His Gln Asn Ala Ala Val Ser Glu Asn Gln Asn His Asp Asp
  1               5                  10                  15

Gly Ala Ala Ser Ser Pro Gly Phe Lys Leu Val Gly Phe Ser Lys Phe
                20                  25                  30

Val Arg Lys Asn Pro Lys Ser Asp Lys Phe Lys Val Lys Arg Phe His
            35                  40                  45
```

-continued

```
His Ile Glu Phe Trp Cys Gly Asp Ala Thr Asn Val Ala Arg Arg Phe
    50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
                85                  90                  95

Phe Leu Phe Thr Ala Pro Tyr Ser Pro Ser Leu Ser Ala Gly Glu Ile
            100                 105                 110

Lys Pro Thr Thr Thr Ala Ser Ile Pro Ser Phe Asp His Gly Ser Cys
        115                 120                 125

Arg Ser Phe Phe Ser Ser His Gly Leu Gly Val Arg Ala Val Ala Ile
130                 135                 140

Glu Val Glu Asp Ala Glu Ser Ala Phe Ser Ile Ser Val Ala Asn Gly
145                 150                 155                 160

Ala Ile Pro Ser Ser Pro Pro Ile Val Leu Asn Glu Ala Val Thr Ile
                165                 170                 175

Ala Glu Val Lys Leu Tyr Gly Asp Val Val Leu Arg Tyr Val Ser Tyr
            180                 185                 190

Lys Ala Glu Asp Thr Glu Lys Ser Glu Phe Leu Pro Gly Phe Glu Arg
        195                 200                 205

Val Glu Asp Ala Ser Ser Phe Pro Leu Asp Tyr Gly Ile Arg Arg Leu
210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
                245                 250                 255

Asp Val Gly Thr Ala Glu Ser Gly Leu Asn Ser Ala Val Leu Ala Ser
            260                 265                 270

Asn Asp Glu Met Val Leu Leu Pro Ile Asn Glu Pro Val His Gly Thr
        275                 280                 285

Lys Arg Lys Ser Gln Ile Gln Thr Tyr Leu Glu His Asn Glu Gly Ala
290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
                325                 330                 335

Ser Pro Pro Thr Tyr Tyr Gln Asn Leu Lys Lys Arg Val Gly Asp
            340                 345                 350

Val Leu Ser Asp Asp Gln Ile Lys Glu Cys Glu Glu Leu Gly Ile Leu
        355                 360                 365

Val Asp Arg Asp Asp Gln Gly Thr Leu Leu Gln Ile Phe Thr Lys Pro
370                 375                 380

Leu Gly Asp Arg Pro Thr Ile Phe Ile Glu Ile Ile Gln Arg Val Gly
385                 390                 395                 400

Cys Met Met Lys Asp Glu Glu Gly Lys Ala Tyr Gln Ser Gly Gly Cys
                405                 410                 415

Gly Gly Phe Gly Lys Gly Asn Phe Ser Glu Leu Phe Lys Ser Ile Glu
            420                 425                 430

Glu Tyr Glu Lys Thr Leu Glu Ala Lys Gln Leu Val Gly
        435                 440                 445
```